United States Patent
Benford

(10) Patent No.: US 7,465,434 B2
(45) Date of Patent: Dec. 16, 2008

(54) DIAGNOSIS OF BLOOD CLOTS USING FIBRIN-BINDING PROTEINS BOUND WITH CONTRAST AGENTS

(76) Inventor: Jacob Benford, c/o Peters Verny LLP, 425 Sherman Ave., Suite 230, Palo Alto, CA (US) 94306

( * ) Notice: Subject to any disclaimer, the term of this patent is extended or adjusted under 35 U.S.C. 154(b) by 0 days.

(21) Appl. No.: 11/411,256

(22) Filed: Apr. 25, 2006

(65) Prior Publication Data

US 2006/0257389 A1    Nov. 16, 2006

Related U.S. Application Data

(60) Provisional application No. 60/674,369, filed on Apr. 25, 2005.

(51) Int. Cl.
*A61K 49/04* (2006.01)
(52) U.S. Cl. ..................................... 424/9.4
(58) Field of Classification Search ............... None
See application file for complete search history.

(56) References Cited

U.S. PATENT DOCUMENTS

| | | | |
|---|---|---|---|
| RE32,271 E | 10/1986 | Husain et al. | |
| 4,636,380 A | 1/1987 | Wong | |
| 5,811,265 A | 9/1998 | Quertermous et al. | |
| 6,808,698 B1 | 10/2004 | Lazewatsky | |
| 6,984,373 B2 | 1/2006 | Wescott et al. | |

OTHER PUBLICATIONS

Liau et al. J Formosan Med Assoc 1989;88(3):209-212.*
Botnar et al. Circulation 2004;109:2023-2029.*
De Bruyn et al. "Visualization of thrombi in pulmonary arteries with radiolabeled, enzymatically inactivated tissue-type plasminogen activator" Circulation, 1995, 92:1320-1325.*
Carroll et al. "Antiangiogenic activity of a domain deletion mutant of tissue plasminogen activator containing Kringle 2", Arterioscler Thromb Vasc Biol. 2005, 25:736-741.*

* cited by examiner

*Primary Examiner*—Jon P Weber
*Assistant Examiner*—Bin Shen
(74) *Attorney, Agent, or Firm*—Peters Verny LLP

(57) ABSTRACT

This invention describes how to modify a fibrin-binding protein, such as tPA, with a contrast agent, such as iodine. This substance could then be given to a patient suspected of having a blood clot by an intravenous route, and then detected by a radiographic study at a short pre-determined time later. Appropriate therapy is started immediately as determined by the radiographic study.

15 Claims, 11 Drawing Sheets

DIAGNOSIS OF BLOOD CLOTS USING FIBRIN-BINDING PROTEINS BOUND WITH CONTRAST AGENTS

CROSS-REFERENCE TO RELATED APPLICATIONS

This application claims the benefit of U.S. Ser. No. 60/674,369, filed Apr. 25, 2005, which is incorporated herein by reference in its entirety.

STATEMENT OF GOVERNMENTAL SUPPORT

None.

BACKGROUND OF THE INVENTION

1. Field of the Invention

This invention describes how to modify a fibrin-binding protein, such as tPA, to produce a fibrin-binding protein without fibrinolytic activating properties. This modified protein is then combined (and/or covalently bonded) with a contrast agent, such as iodine. This combination substance is then administered to a patient suspected of having a blood clot by a standard route. Next, any blockage or clot is detected by a radiographic study at a short pre-determined time later, and the patient is immediately treated with drugs and/or therapy based on the diagnosis/results of the radiographic study.

2. Related Art

Background

Currently, there are numerous tests that may be used when trying to detect a blood clot in a patient. Unfortunately all of these methods have limitations, such as high radiation load or nephrotoxicity, and many are not sensitive enough for clinical practice. Problems also arise concerning storing and disposing radioactive material when using some tests.

Relevant Literature

The following U.S. patents are relevant to this invention:

Rhodes, et al., "Radiopharmaceuticals for Localization of Thromboembolic Disease," U.S. Pat. No. 4,416,865 (November, 1983).

Moser, et al., "Methods and Compositions for the Diagnosis of Bloodclots Using Plasminogen Activator," U.S. Pat. No. 4,663,146 (May, 1987).

Reno, et al., "Method of Diagnosing Blood Clots Using Fibrin-Binding Proteins," U.S. Pat. No. 5,217,705 (June, 1993).

Rhodes, et al., "Direct Labeling of Antibodies and Other Protein With Metal Ions," U.S. Pat. No. 5,460,785 (October, 1995).

Rhodes, et al., "Direct Labeling of Peptides With Metal Ions," U.S. Pat. No. 5,861,139 (January, 1999).

The U.S. patents and patent applications cited are incorporated herein by reference in their entirety.

It can be seen with a review of the art that problems remain to quickly diagnose and quickly treat blockages in the blood vessel where time is of the essence for mammals, particularly humans. The present invention describes some solutions to this problem.

BRIEF SUMMARY OF THE INVENTION

This invention describes the steps to modify a fibrin-binding protein and then combine this with a contrast agent. The contrast agent may be a single ion, or a molecule of a pre-formulated contrast agent. This compound is then given through an IV to a patient suspected of having a blood clot (see FIGS. 1-9). After waiting a sufficient amount of time for the compound to circulate and to bind the suspected blood clot, a radiographic study (plain x-ray or CT) is then obtained. A "hot spot" or collection of the contrast agent seen on the radiographic study would represent the presence and location of a blood clot (FIGS. 10-11). As blood vessels would not need to be filled with the contrast agent, relatively small amounts of this compound are used, thus limiting side effects. The results are also quickly and easily interpreted by a clinician, without the need for specialized personnel or equipment for administration and interpretation.

DETAILED DESCRIPTION OF THE INVENTION AND PREFERRED EMBODIMENTS

Figure 1:
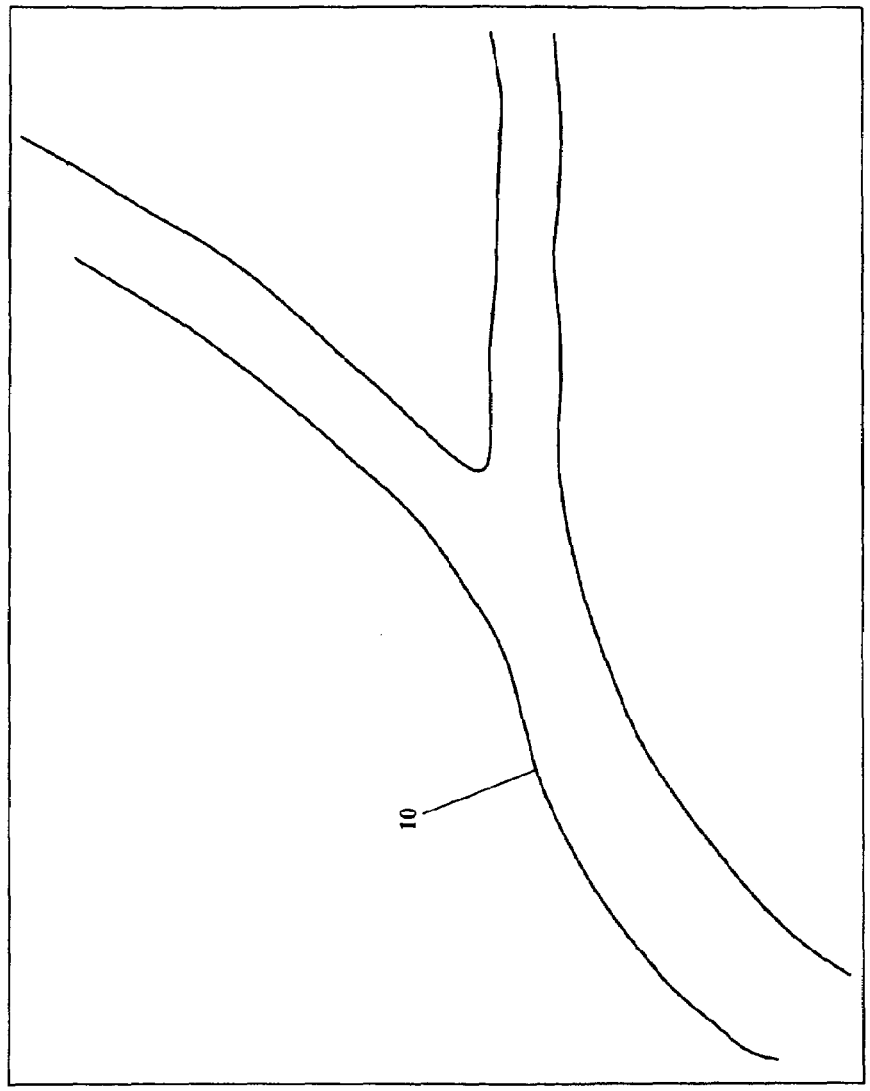
FIG. 1 is a cross sectional schematic representation of a normal blood vessel shown as a branched structure.
Figure 2:
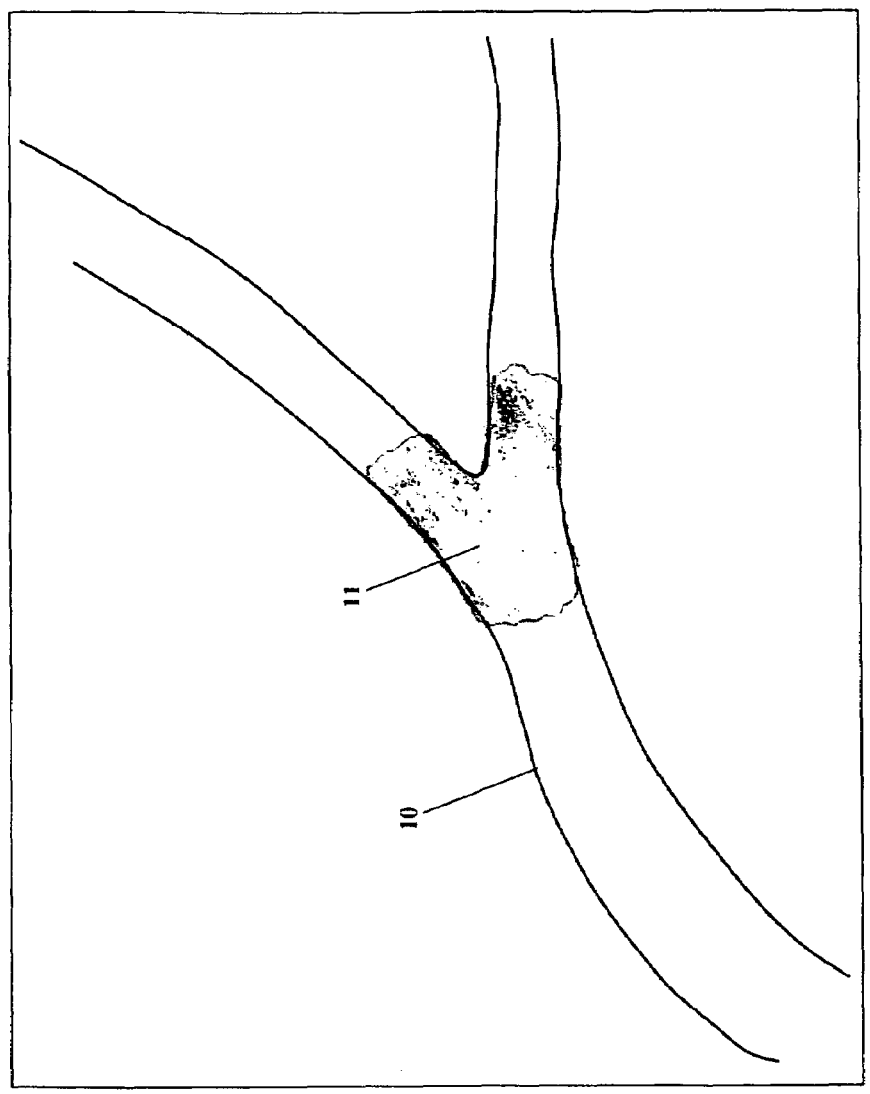
FIG. 2 is cross sectional schematic representation of a branched blood vessel having blood flow occluded by an embolus.

In this document, the term:

"Blush" refers to an area of brightness that is seen on a radiographic study that represents a concentration of contrast material.

"Contrast agent" is used to describe a substance that improves the visibility of structures during a radiographic study.

"CT" is used to describe a computed tomography, which is a radiographic study by which x-ray slices of the body are taken with a scanning machine, and then reformatted by a computer to give cross sectional images of the body.

"Fibrin" is used to describe an end product in the formation of a blood clot. Fibrinogen is converted to fibrin by thrombin, which acts as an interlacing mesh. This mesh then forms a clot with red and white blood cells and platelets sticking to the interlacing mesh.

"Hot spot" is used to describe a bright area seen on a radiographic image, representing a concentration of contrast material.

"MRI" is used to describe magnetic resonance imaging. This is a radiographic study that utilizes the principle of nuclear magnetic resonance to generate images of the body. With this method, the patient is passed through a magnetic field, a short pulse of radio frequency energy is applied to the patient, and a computer utilizes the voltage that is produced by the cell in response to the radio frequency energy to produce images.

Numerous methods of modifying a plasmid to obtain a modified protein have been previously described, and many are marketed commercially as kits, for example, by Pierce, 3747 N. Meridian Rd., PO Box 117, Rockford, Ill. 61105. Any of these methods may be used when modifying the fibrin binding protein.

In one embodiment of the invention, the Gateway method of plasmid modification is used. In this method, a plasmid for tPA is modified with a cleaving enzyme, such as XHO1. By performing a site-specific mutagenesis in the coding sequence of CTCGAG, which is in the QPQ region of amino acid #272, a XHO1 cleaving site is created. In doing this, the coding sequence after approximately amino acid 273 is deleted, and thus creating a plasmid that will express a fibrin binding protein that does not have the serine protease domain. The serine protease domain is responsible for activating the fibrinolytic cascade. The coding sequence for the remaining N-terminal domains of the protein is fused with a sequence encoding a His tag. This is accomplished by recombining the clone containing the modified tPA coding sequence with a destination plasmid, such as pcDNA-DEST40. This new plasmid is then transverted into a cell line, such as F293 mammalian cells, and incubated to produce the modified protein. This protein is then purified utilizing the histine tag.

In one embodiment of the invention, the modified protein is iodinated with IODO-GEN pre-coated tubes and a Tris Iodination Buffer. Utilizing the steps described in the kit, the solution is then washed through desalting columns, such as the Pierce D-Salt Polyacrylamide 6000 Desalting Columns, to isolate the iodinated protein.

In another embodiment of the invention, the modified protein is bound or linked to paramagnetic metal chelates, which are utilized as contrast agents for MRI scanning. These paramagnetic metals include, but are not limited to, Gd, Fe, Mn, Cr, Cu and Eu. The organic chelator has polar groups that help to act as a ligand, or bridge, between the protein and paramagnetic agent. These chelators, which are well established in the art, include, but are not limited to DTPA, EDTA and TETA. Further, these chelators are bound directly to the fibrin binding protein, or a linker, such as an amide, urea, acetal, or phosphodiester. This binding is best suited to occur at the N or C terminus, but placed in any position that did not interfere with the Kringle domains and the fibrin binding.

In still another embodiment of the invention, the modified protein is linked to materials used as contrast agents for ultrasound. These materials require them to be echogenic, and include, but are not limited to various gases and natural and synthetic materials. These materials and the binding to the protein are well described and established in the art.

Other agents that act as contrast agents include radioactive agents, including but not limited to iodine, to be used in nuclear imaging and PET scanning, or photolabels, to be used in optical imaging. These agents and their binding to proteins is also well described and established in the art.

The modified protein of this invention combined with a contrast agent is administered to patients suspected of having a blood clot as a 50 mg bolus infusion. After a waiting period of 5-10 minutes, the patient undergoes a radiographic evaluation, without further contrast. A blood clot is identified on the radiograph by a single contrast "blush" in the area of the blood clot.

The invention is also described as follows:

The fibrin-binding protein (for example. Alteplase, TNK, Reteplase, Streptokinase, and combinations thereof) is coupled with the contrast agent as described herein. The kit for administration with various instructions is created.

Figure 4:
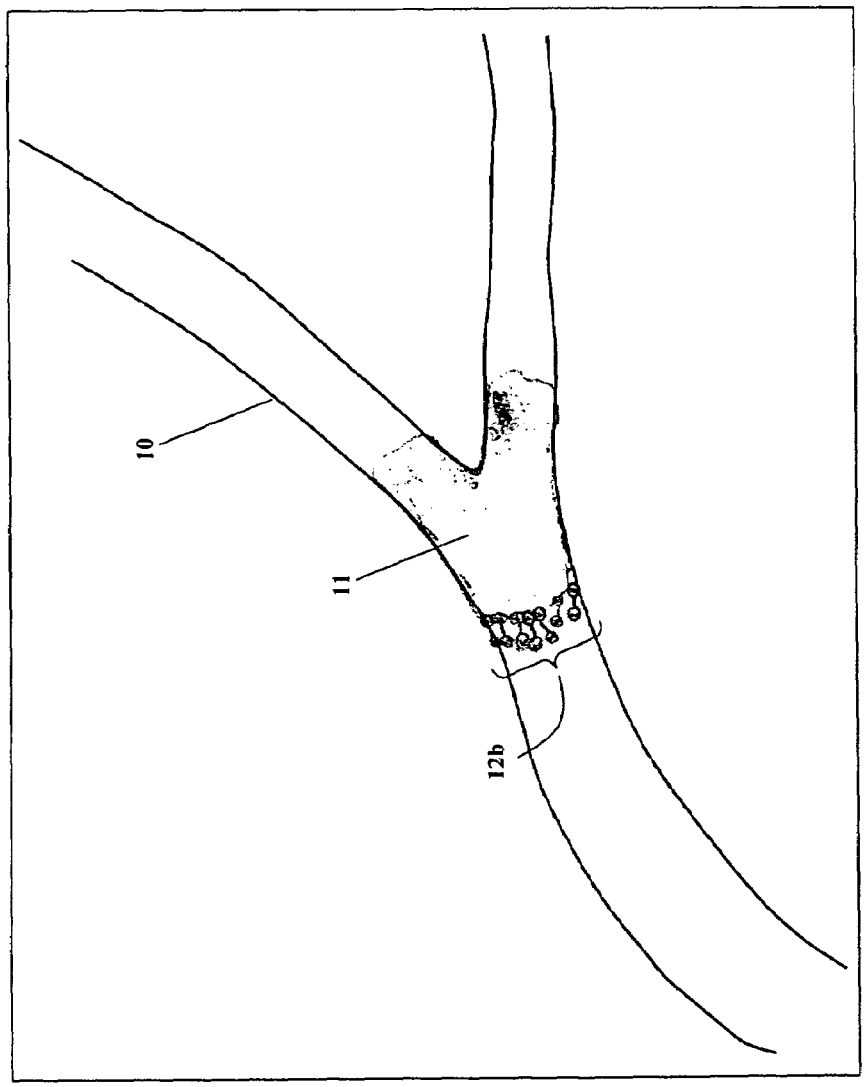
FIG. 4 is a cross sectional schematic representation of a branched blood vessel with an embolus occluding blood blow and the fibrin-binding protein-contrast agent bound to the embolus after about ten minutes.

FIG. 4 is a cross sectional schematic representation of a branched blood vessel with an embolus occluding blood flow and the fibrin-binding protein-contrast agent bound to the embolus after about ten minutes.

Figure 3:
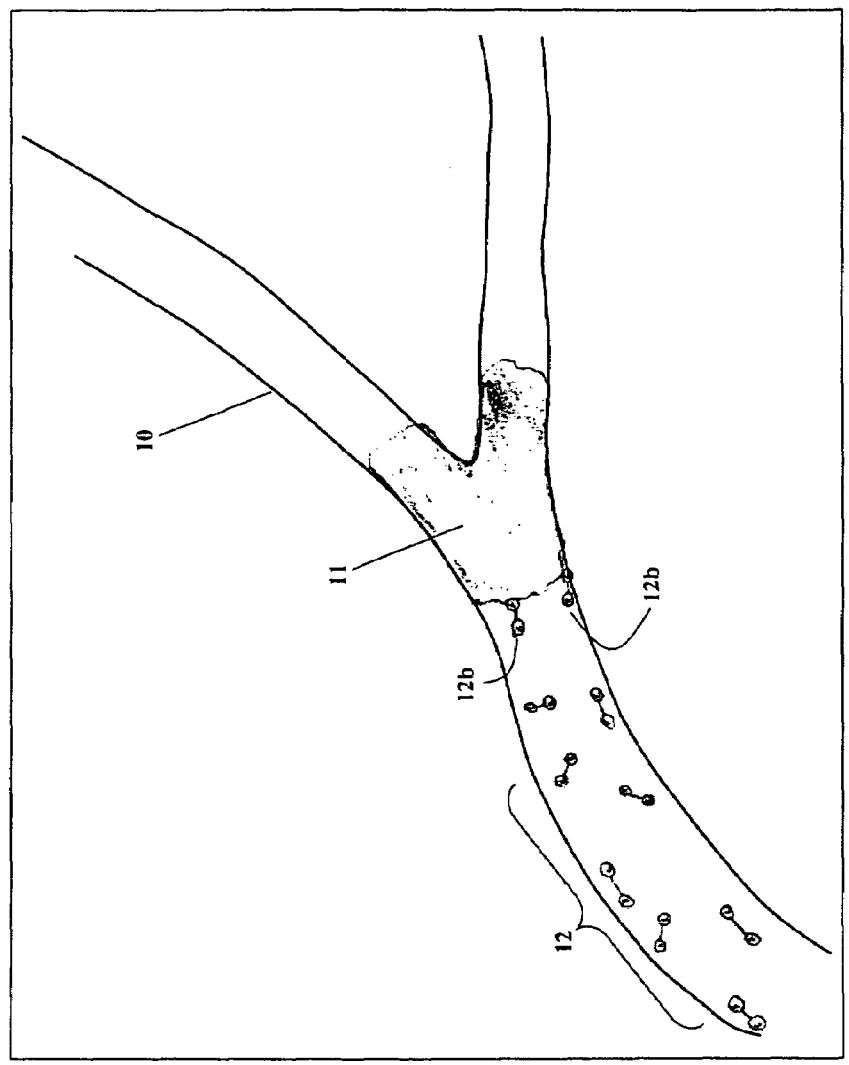
FIG. 3 is a cross sectional schematic representation of a branched blood vessel with an embolus occluding blood flow and the fibrin-binding protein-contract agent recently added.

The injection of a quantity of the fibrin-binding protein contrast agent compound (12) occurs as shown in FIG. 3. Note that only a small amount of the compound (12b) binds to the surface of the fibrin of the embolus (11).

In FIG. 4 about 10 minutes after the fibrin-binding protein-contrast agent has been administered, changes are observed. The fibrin-binding protein-contrast agent has now bound to the embolus (11) in sufficient quantity to be identified by a radiographic image. The unbound compound is washed away in the blood stream or is metabolized.

Figure 5:
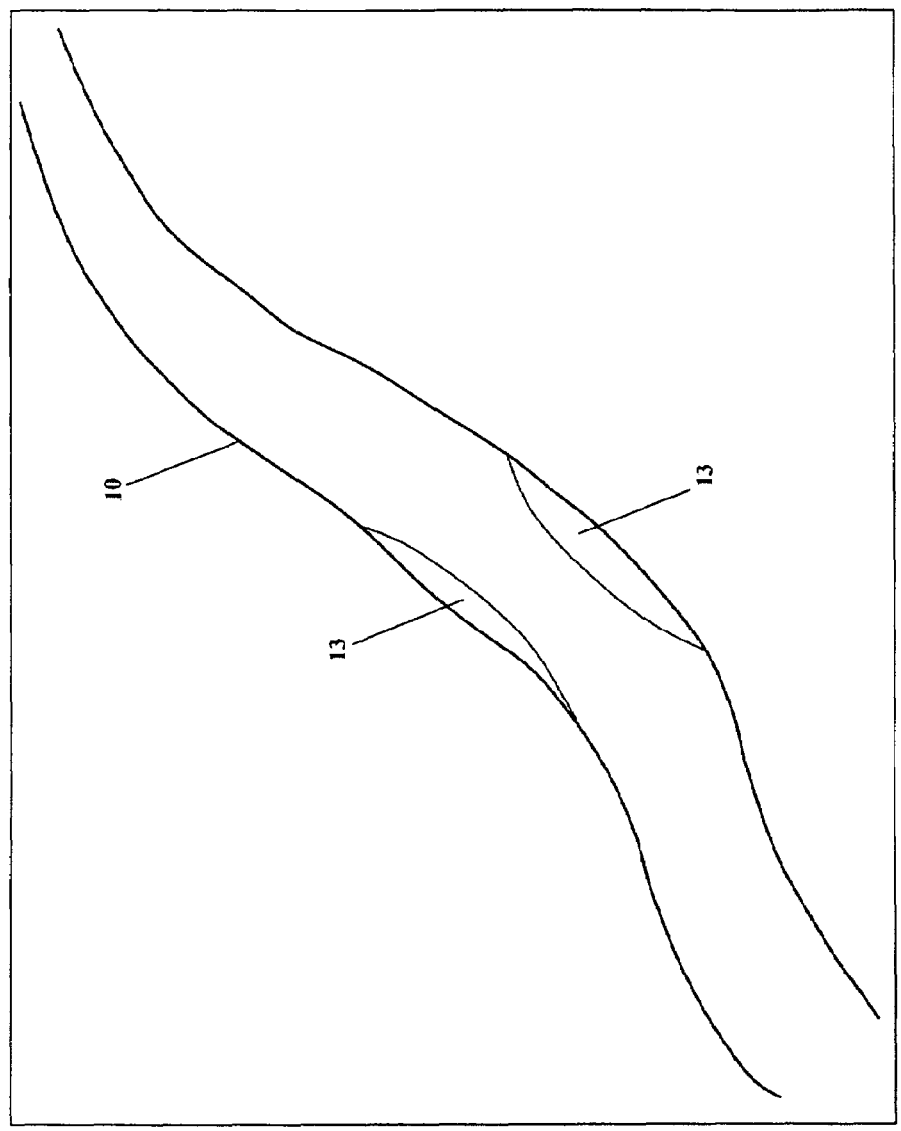
FIG. 5 is a cross sectional schematic representation of a blood vessel with an unstable plaque.
Figure 6:
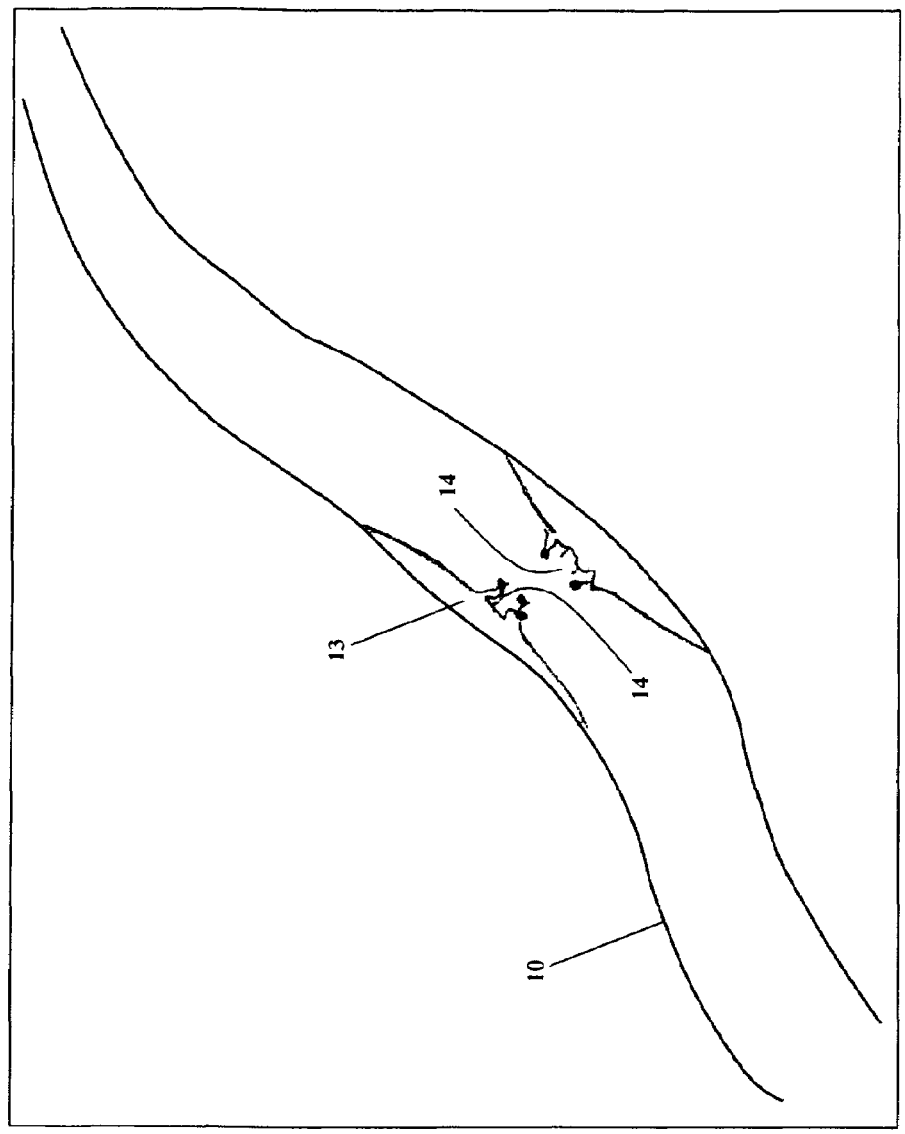
FIG. 6 is a cross sectional schematic representation of a blood vessel after plaque rupture.
Figure 7:
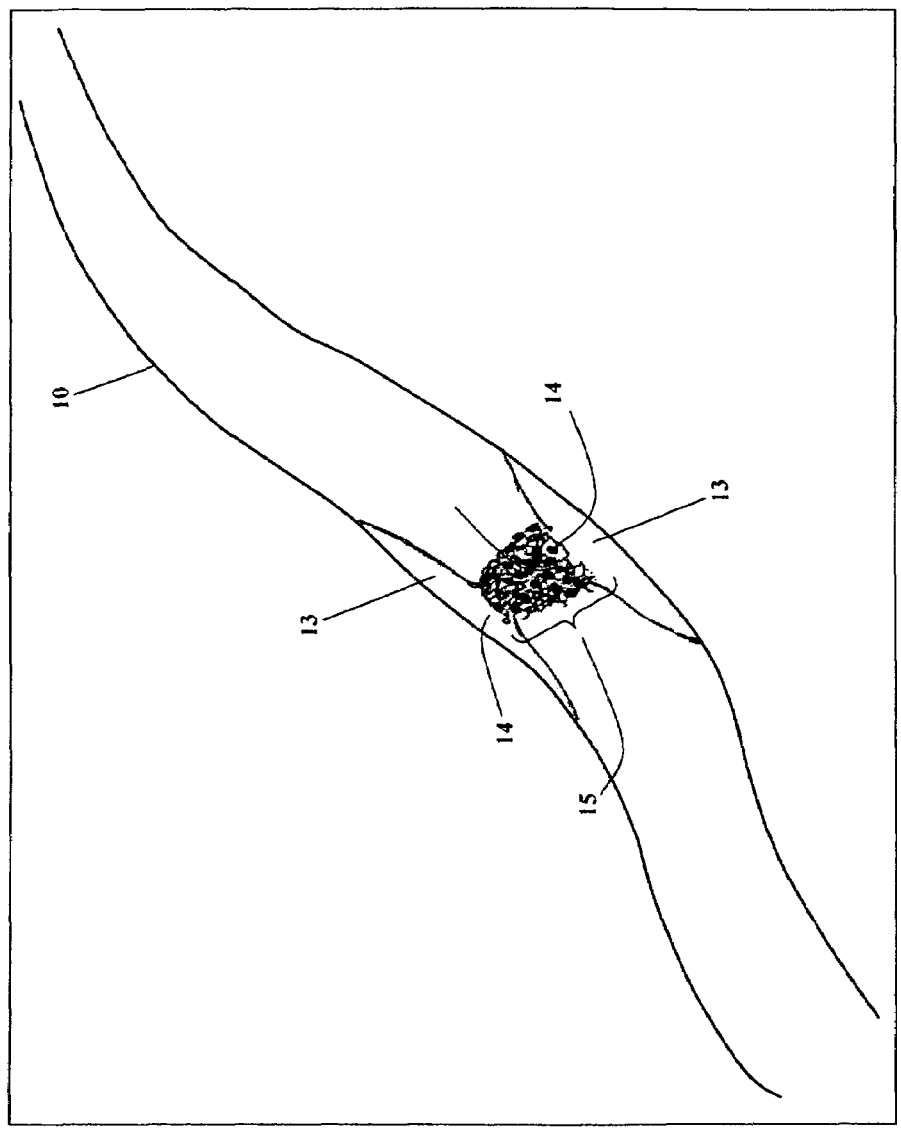
FIG. 7 is a cross sectional schematic representation of a blood vessel showing plaque rupture and thrombus formation.
Figure 8:
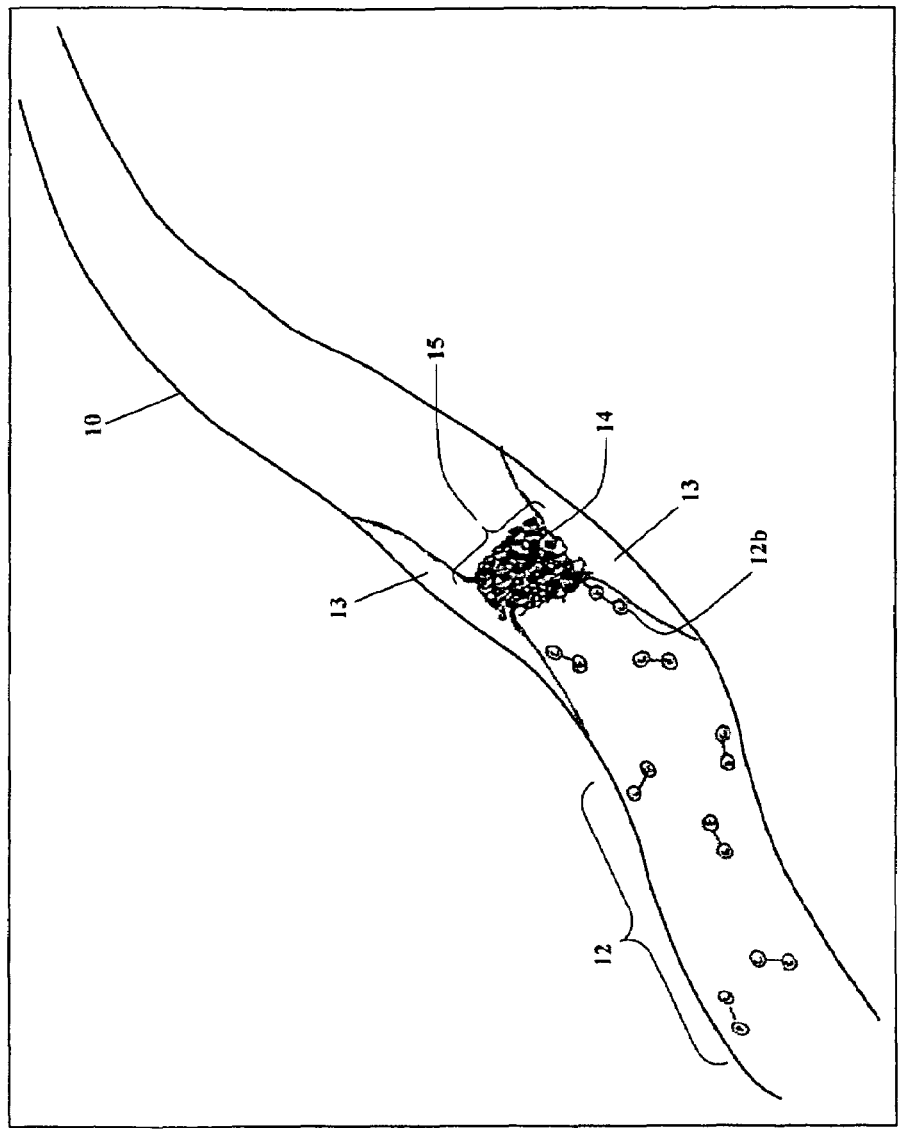
FIG. 8 is a cross sectional schematic representation of a blood vessel with plaque rupture and thrombus formation shortly after administration of binding protein-contrast agent. The binding protein-contrast agent is partially bound.
Figure 9:
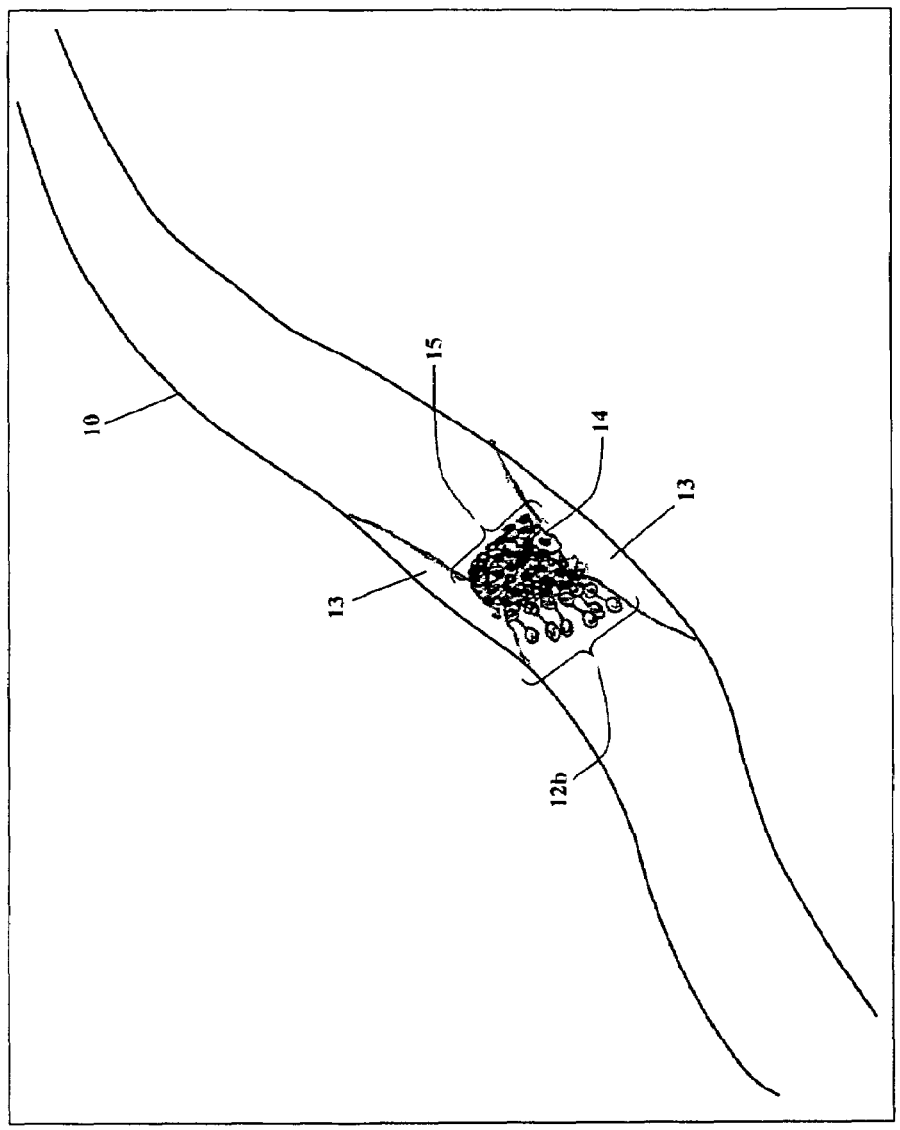
FIG. 9 is a cross sectional schematic representation of a blood vessel with plaque rupture and thrombus formation approximately 10 minutes after administration of binding protein-contrast agent. The binding protein-contrast agent is now extensively bound to the thrombus.

FIG. 5 shows a blood vessel (10) with an unstable plaque deposit (13) and FIG. 6 shows the situation with plaque rupture (14). FIG. 7 combines FIGS. 5 and 6 with the formation of a thrombus (15). After administration as shown in FIG. 8, fibrin-binding protein-contrast agent 12 is present and some is partially bound (12b) to the thrombus (15). FIG. 9 shows the compound (12) bound to the thrombosis (15) in sufficient quantity (12b) to be identified in a radiological analysis. The remaining free compound 12 is washed away or is metabolized.

Figure 10:
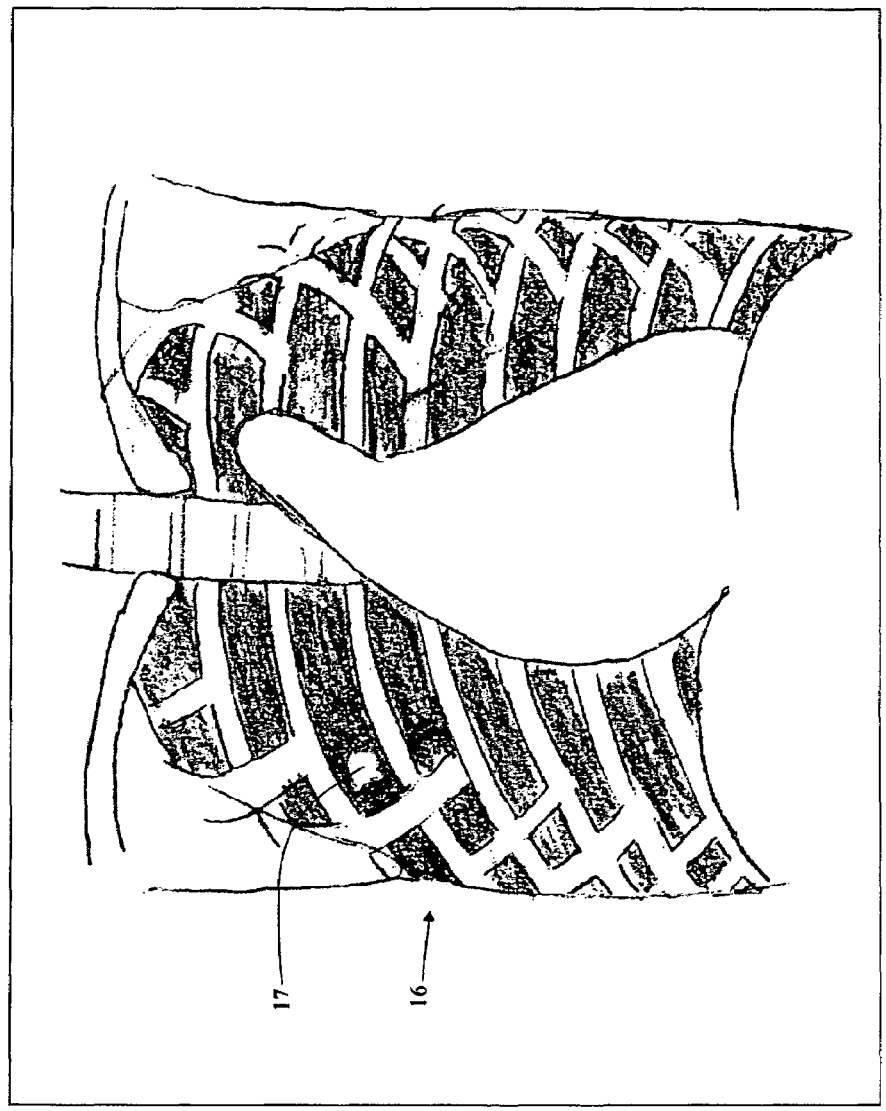
FIG. 10 is a schematic representation of a chest x-ray approximately 5-10 minutes after fibrin-binding protein-contrast agent has bound to a blood clot in the lung. The "blush" of the contrast can be seen in the right upper lobe.

FIG. 10 is a schematic representation of a chest x-ray (16) after fibrin-binding protein contrast agent bound to a blood clot located in the right upper lung lobe. Identification of the blood clot is made visually by the "blush" or white spot (17) noted in the upper right lobe.

Figure 11:
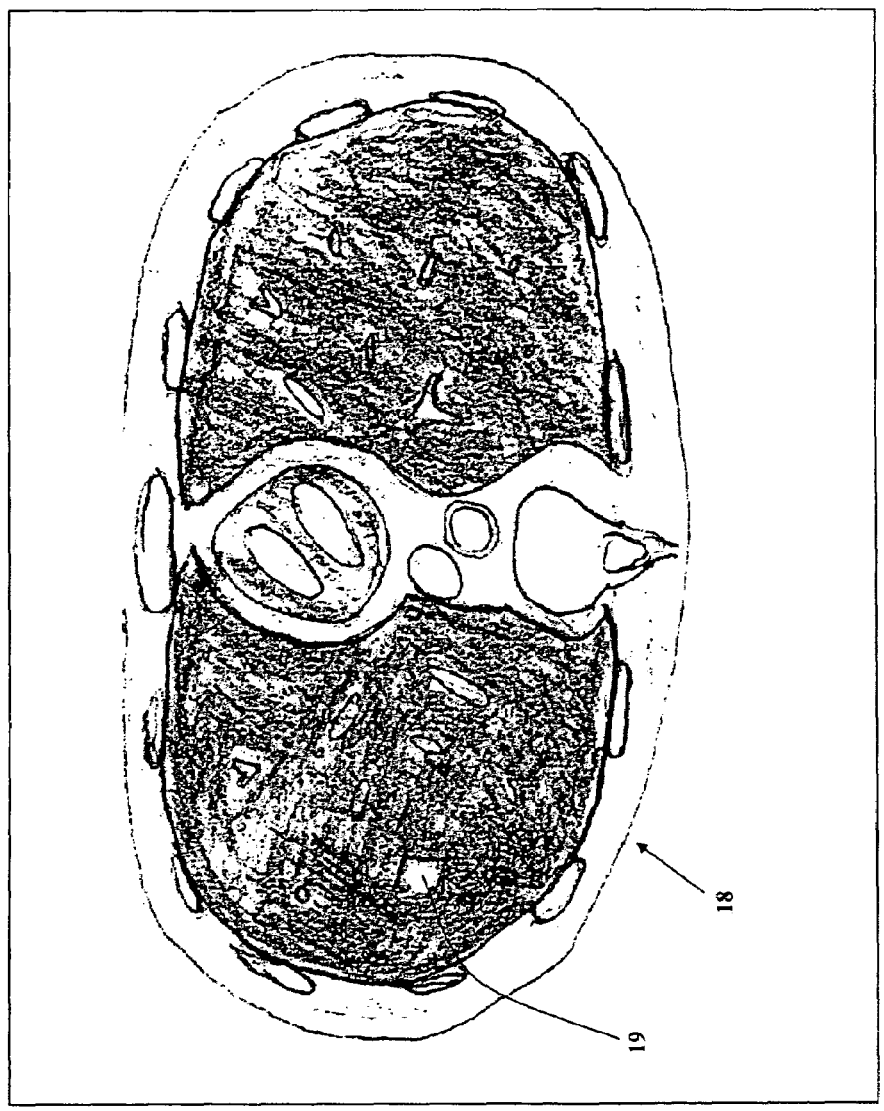
FIG. 11 is a schematic representation of a CT scan of the chest approximately 5-10 minutes after fibrin-binding protein-contrast agent has bound to a blood clot in the lung. The "blush" of the contrast can be seen in the right upper lobe.

FIG. 11 is a schematic image depicting a CAT scan of the chest (18) taken after fibrin-binding protein-contrast agent bound to a blood clot in the upper right lobe. The blood clot is identified by the "blush" or white spot (19) in the upper right lobe on the CAT scan.

EXPERIMENTAL

General Methods

The general methods described herein in this invention for cleaving of protein at a specific site and for covalent bonding with a specific contrast moiety are well known in the art and are adapted and combined as described.

The starting materials are obtained from commercial chemical and biochemical supply however. Some kits used were from Invitrogen, 1600 Faraday Ave., Carlsbad, Calif. 92008.

The solvents and reagents used herein are available from commercial sources. See those listed in Chemical Sources, USA, published annually by Chemical Sources International, Inc., in Clemson, S.C. and on the Internet.

Unless specifically noted all materials are used without further purification.

Administration

In the practice of the method of this invention, an effective amount of a compound of the invention or a pharmaceutical composition containing same is administered to the subject in need of, or desiring, such treatment. These compounds or compositions may be administered by any of a variety of routes depending upon the specific end use, primarily intravenous administration. The most suitable route in any given case will depend upon the use, particular active ingredient, the subject involved, and the judgment of the medical practitioner.

In general, for the uses hereinabove described, it is expedient to administer the active ingredient in amounts between about 0.001 and 100 mg/kg body weight, preferably between about 0.05 and 5.0 mg/kg body weight. The exact dose and regiment for administration of these compounds and compositions will necessarily be dependent upon the needs of the individual subject being treated. A further aspect of the present invention relates to pharmaceutical compositions containing as active ingredient a compound of the present invention which compositions comprise such compound in admixture with a pharmaceutically acceptable non-toxic carrier.

The compositions may conveniently be administered in unit dosage form and may be prepared by any of the methods well-known in the pharmaceutical art, for example as described in Remington's Pharmaceutical Sciences, Mack Publishing Co. Easton Pa., 1970. Formulations for intravenous administration may contain as common excipients sterile water or saline, polyalkylene glycols such as polyethylene glycol, oils of vegetable origin, hydrogenated naphthalenes and the like. Also see and adapt the description in U.S. Pat. No. 4,318,905.

EXAMPLE 1

Detection of Blocked Blood Vessel

A 45-year-old male presents with substernal chest pain. He has a complex medical history, and possible etiologies for his pain include an acute heart attack, a pulmonary embolus, or his chronic pulmonary disease. His initial ECG in non-diagnostic. In addition to standard treatment, the fibrin-binding protein-contrast agent 50 mg/kg is given as a bolus intravenous injection. After 10 minutes a CT of his chest is preformed which shows a "blush" of contrast in the area of the heart, consistent with a blocked coronary blood vessel. The patient is then quickly seen by the cardiologist and definitive treatment (e.g., tPA) is given without delay.

EXAMPLE 2

Detection of Pulmonary Embolus

A 75-year-old female presents with shortness of breath. The patient has a long history of smoking, and has a slight fever on presentation. She has just returned from vacation, which included a 6-hour trip. The fibrin-binding protein-contrast agent compound is given as a bolus intravenous injection. 10 minutes later, a chest x-ray is taken that is clear except for a slight blush in the right middle lobe. She is then taken to the CT scan, which shows a contrast "blush" in the right middle lobe, consistent with a blood clot, or pulmonary embolus. The patient is admitted for definitive treatment.

EXAMPLE 3

Detection of Blood Clot in Leg Vessel

A 28-year-old male presents with increasing swelling and pain of his left leg. The patient broke the same leg three weeks ago, and it is now in a cast. The patient was doing well, with minimal pain until four days ago. His exam is normal except for mildly swollen toes at the far end of his cast. The fibrin-binding protein-contrast agent compound is administered by intravenous bolus to his descending artery. The patient then has an x-ray of his upper and lower leg 10 minutes later, which shows a contrast "blush" just above the knee. Treatment (e.g., coumidin) is started for the blood clot, and a potential pulmonary embolus is avoided.

EXAMPLE 4

Detection of Cranial Thrombosis

A 58-year-old male presents with sudden onset of right-sided weakness of approximately one-hour duration. This has never happened before, but his father had several strokes before he passed away. The patient's only risk factor is smoking. His symptoms have not changed since onset. He is a candidate for thrombolytic therapy if his CT scan shows a blocked blood vessel. The fibrin-binding protein-contrast agent compound is given by intravenous bolus. The patient has a CT scan of the brain in 10 minutes, which is normal with NO contrast "blush". The patient is not given thrombolytic therapy, which could be harmful, and makes a full recovery.

While only a few embodiments of the invention have been shown and described herein, it will become apparent to those skilled in the art that various modifications and changes can be made in the contrast agent combination structure and features of the compositions of matters, the pharmaceutical compositions, kits, methods of manufacture, or methods of therapy for in vivo migration and concentration of bio molecules and to provide observable contrast agent and determining therapy properties without departing from the spirit and scope of the present invention. All such modifications and changes coming with the scope of the appended claims are intended to be carried out thereby.

I claim:

1. A method for detecting a blood clot in a mammalian patient, the method comprising:
    (a) using a nucleic acid sequence to express a fibrin-binding protein wherein the sequence has been modified to delete a coding sequence that codes for the serine protease domain to remove fibrinolytic activating properties of the fibrin-binding protein;
    (b) producing a compound comprising the fibrin-binding protein and a contrast agent;
    (c) introducing the compound into the patient via bolus by an intravenous or intra-arterial insertion;
    (d) binding the compound to a blood clot; and
    (e) detecting the compound bound to the blood clot using a radiographic study.

2. The method of claim 1 wherein the fibrin-binding protein comprises:
    (a) Alteplase;
    (b) TNK;
    (c) Reteplase;
    (d) Streptokinase, or
    (e) combinations thereof.

3. The method of claim 1 wherein the fibrin-binding protein before modification includes Alteplase.

4. The method of claim 1 wherein the contrast agent includes:
(a) Iodine;
(b) Gadolinium, or combinations thereof.

5. The method of claim 1 wherein the contrast agent includes iodine.

6. The method of claim 1 wherein the contrast agent includes gadolinium.

7. The method of claim 1 wherein the fibrin-binding protein-contrast agent compound is administered to a human being in an amount between about 0.001 and 100 mg/kg.

8. The method of claim 1 wherein the fibrin-binding protein-contrast agent compound is administered to a human being in an amount between 0.25 and 0.75 mg/kg.

9. The method of claim 1 wherein the mammal is a human being.

10. The method of claim 1 wherein the patient is a human being and the fibrin-binding protein-contrast agent compound is administered to the human being in an amount between about 0.05 and 5 mg/kg.

11. The method of claim 1 wherein detecting the compound occurs about 5-10 minutes after introducing the compound into the patient.

12. The method of claim 1 wherein the radiographic study includes an x-ray.

13. The method of claim 1 wherein the radiographic study includes computed tomography.

14. The method of claim 1 wherein the nucleic acid sequence is a naturally occurring nucleic acid sequence.

15. A method for detecting a blood clot in a mammalian patient, the method comprising:
(a) using a nucleic acid to express a fibrin-binding protein wherein a sequence of the nucleic acid has been modified to delete a coding sequence that codes for the serine protease domain to remove fibrinolytic activating properties of the fibrin-binding protein;
(b) producing a compound comprising the fibrin-binding protein and a contrast agent;
(c) introducing the compound into the patient via bolus by an intravenous or intra-arterial insertion;
(d) binding the compound to a blood clot; and
(e) detecting the compound bound to the blood clot using a radiographic study.

* * * * *